(12) United States Patent
Niu et al.

(10) Patent No.: US 11,155,793 B2
(45) Date of Patent: Oct. 26, 2021

(54) PHYTASE VARIANTS YEAPPA HAVING IMPROVED GASTRIC PROTEIN RESISTANCE AND ACID RESISTANCE, AND INCREASED CATALYTIC EFFICIENCY

(71) Applicants: FEED RESEARCH INSTITUTE CHINESE ACADEMY OF AGRICUL, Beijing (CN); Canfang Niu, Beijing (CN); Peilong Yang, Beijing (CN); Bin Yao, Beijing (CN); Yangyang Li, Beijing (CN); Yongkai Du, Beijing (CN); Huiying Luo, Beijing (CN); Huoqing Huang, Beijing (CN); Yaru Wang, Beijing (CN)

(72) Inventors: Canfang Niu, Beijing (CN); Peilong Yang, Beijing (CN); Bin Yao, Beijing (CN); Yangyang Li, Beijing (CN); Yongkai Du, Beijing (CN); Huiying Luo, Beijing (CN); Huoqing Huang, Beijing (CN); Yaru Wang, Beijing (CN)

( * ) Notice: Subject to any disclaimer, the term of this patent is extended or adjusted under 35 U.S.C. 154(b) by 0 days.

(21) Appl. No.: 16/477,903

(22) PCT Filed: Jan. 15, 2018

(86) PCT No.: PCT/CN2018/072540
§ 371 (c)(1),
(2) Date: Jul. 15, 2019

(87) PCT Pub. No.: WO2018/130211
PCT Pub. Date: Jul. 19, 2018

(65) Prior Publication Data
US 2020/0140833 A1    May 7, 2020

(30) Foreign Application Priority Data

Jan. 15, 2017   (CN) .......................... 201710027074.8

(51) Int. Cl.
| | | |
|---|---|---|
| *C12N 9/16* | (2006.01) | |
| *C12N 1/21* | (2006.01) | |
| *C12N 15/55* | (2006.01) | |
| *A23K 20/189* | (2016.01) | |
| *C12N 15/52* | (2006.01) | |
| *C12N 15/70* | (2006.01) | |

(52) U.S. Cl.
CPC .............. *C12N 9/16* (2013.01); *A23K 20/189* (2016.05); *C12N 15/52* (2013.01); *C12N 15/70* (2013.01); *C12Y 301/03008* (2013.01)

(58) Field of Classification Search
None
See application file for complete search history.

(56) References Cited

U.S. PATENT DOCUMENTS

| 8,455,620 B2 * | 6/2013 | Yao .......................... C12N 9/16 |
| --- | --- | --- |
| | | 530/350 |
| 2010/0192985 A1 * | 8/2010 | Aehle ................ C11D 3/38645 |
| | | 134/26 |

FOREIGN PATENT DOCUMENTS

| CN | 106011101 A | | 10/2016 |
|---|---|---|---|
| CN | 106119223 A | | 11/2016 |
| CN | 106191000 A | * | 12/2016 |
| CN | 106591256 A | * | 4/2017 |

OTHER PUBLICATIONS

Huang et al., Biochem. Biophys. Res. Commun. 350:884-889, 2006 (Year: 2006).*
Zhang et al., Structure 26:1474-1485, 2018 (Year: 2018).*
UniProt Database Accession No. A0A481QK21, Dec. 2019, 1 page (Year: 2019).*
Niu et al., Sci. Rep. 7:42133, Feb. 2017, 14 pages (Year: 2017).*
Machine translation of CN106591256A, obtained from Google patents on Mar. 26, 2021, 9 pages (Year: 2021).*
ISR; State Intellectual Property Office of the PR China; Beijing; Mar. 19, 2018.
Niu, C. F. et al. Engineering the Residual Side Chains of HAP Phytases to Improve Their Pepsin Resistance and Catalytic Efficiency. Scientific Reports; Feb. 10, 2017.
Niu, C.F. et al. N-Glycosylation Improves the Pepsin Resistance of Histidine Acid Phosphatase Phytases by Enhancing Their Stability at Acidic PHS and Reducing Pepsin's Accessibility to Its Cleavage Sites. Applied and Enviornmental Microbiology; Jun. 29, 2016.

* cited by examiner

*Primary Examiner* — David Steadman
(74) *Attorney, Agent, or Firm* — Patshegen IP LLC; Moshe Pinchas (57) ABSTRACT

The present invention relates to the field of genetic engineering, particularly to phytase variant YeAPPA having improved pepsin resistance and acid resistance, and increased catalytic efficiency, by substituting Leucine at the $162^{th}$ site of the sequence set forth in SEQ ID NO.1 with glycine or proline or substituting glutamic acid at the $230^{th}$ site of the sequence set forth in SEQ ID NO.1 with glycine, proline or arginine, in the benefit of the development of economical feed enzyme industry.

6 Claims, 1 Drawing Sheet
Specification includes a Sequence Listing.

PHYTASE VARIANTS YEAPPA HAVING IMPROVED GASTRIC PROTEIN RESISTANCE AND ACID RESISTANCE, AND INCREASED CATALYTIC EFFICIENCY

FIELD OF THE INVENTION

The present invention relates to the field of genetic engineering, particularly to phytase variants YeAPPA having improved pepsin resistance and acid resistance, and increased catalytic efficiency.

BACKGROUND OF THE INVENTION

Phytase can hydrolyze phytic acid into phosphoric acid residues to destroy the binding of phytic acid to mineral elements, and thus improve the utilization rate of nutrients. Therefore, phytase with high catalytic efficiency and protease resistance can produce good economic and ecological benefits, and will have a broad market in feed industry.

The catalytic function of phytase is directly related to its molecular structure. The study of the crystal structure of the different phytases will be able to help us to deepen understanding of the structure and function of phytases. At present, the crystal structures of several phytases with distinct structures have been reported. The phytases molecule consists of some structural components necessary for catalysis, and some unnecessary components which can be modified to adapt to hydrolyze the different substrates.

Order of the Invention

One order of the present invention is to provide phytase variants having improved pepsin resistance and acid resistance, and increased catalytic efficiency by a method of site-directed mutagenesis.

Another order of the present invention is to provide a gene encoding the above phytase variants having improved pepsin resistance and acid resistance, and increased catalytic efficiency.

Another order of the present invention is to provide a recombinant vector comprising the above gene encoding the above phytase variants having improved pepsin resistance and acid resistance, and increased catalytic efficiency.

Another order of the present invention is to provide a recombinant cell comprising the above gene encoding the above phytase variants having improved pepsin resistance and acid resistance, and increased catalytic efficiency.

SUMMARY OF THE INVENTION

One aspect of the present invention is to provide a site-directed mutation variants of phytase of which the mature protein has amino acid sequence as set forth in SEQ ID NO.1, encoded by SEQ ID NO.2. The material in the ASCII text file named "AmendedFileJan6-20" (35 KB) which was created on Jan. 6, 2020, is incorporated herein by reference.

According to the present invention, said phytase variants YeAPPA having improved pepsin resistance and acid resistance, and increased catalytic efficiency are obtained by mutation at the $162^{th}$ site of Leucine into glycine or alanine, or the $230^{th}$ site of glutamic add into glycine, proline or arginine for phytase with amino acid as set forth in SEQ ID NO.1.

According to the present invention, five phytase variants with having improved pepsin resistance and acid resistance named as YeAPPA-L162G, YeAPPA-L162A, YeAPPA-E230G, YeAPPA-E230P, and YeAPPA-E230R are obtained by site-directed mutation of the $162^{th}$ site of Leucine into glycine or alanine, or the $230^{th}$ site of glutamic acid into glycine, pro line or arginine for phytase with amino acid as set forth in SEQ ID NO.1.

According to embodiment of the present invention, the phytase variant YeAPPA-L162G with amino acid sequence as set forth in SEQ ID NO.3 is obtained by mutation at the $162^{th}$ site of Leucine into glycine for phytase with amino add as set forth in SEQ ID NO.1.

According to embodiment of the present invention, the phytase variant YeAPPA-L162A with amino acid sequence as set forth in SEQ ID NO.4 is obtained by mutation at the $162^{th}$ site of Leucine into alanine for phytase with amino acid as set forth in SEQ ID NO.1.

According to embodiment of the present invention, the phytase variant YeAPPA-E230G with amino acid sequence as set forth in SEQ ID NO.5 is obtained by mutation at the $230^{th}$ site of glutamic acid into glycine for phytase with amino acid as set forth in SEQ ID NO.1.

According to embodiment of the present invention, the phytase variant YeAPPA-E230P with amino acid sequence as set forth in SEQ ID NO.6 is obtained by mutation at the $230^{th}$ site of glutamic acid into proline for phytase with amino acid as set forth in SEQ ID NO.1.

According to embodiment of the present invention, the phytase variant YeAPPA-E230R with amino acid sequence as set forth in SEQ ID NO.7 is obtained by mutation at the $230^{th}$ site of glutamic acid into arginine for phytase with amino acid as set forth in SEQ ID NO.1.

Another aspect of the invention is to provide a gene encoding the above phytase variants having improved pepsin resistance and acid resistance, and increased catalytic efficiency, with nucleotide sequence as set forth in SEQ ID NO.8, SEQ ID NO.9, SEQ ID NO.10, SEQ ID NO.11, and SEQ ID NO.12 respectively.

Another aspect of the invention is to provide a recombinant vector comprising polynucleotides encoding above phytase variants, preferably provide a recombinant E coli. expressing vector comprising the genes encoding phytase variants inserted between sites EcoRI and NotI as so to be controlled under the promoter T7-lac.

Yet another aspect of the invention is to provide a recombinant host cell comprising polynucleotides encoding above phytase variants, and preferably provide a recombinant E coli host, recombinant E coli BL21 (DE3).

Phytase variants of the present invention have the improved pepsin resistance and acid resistance, and the catalytic efficiency increased by 1.6 times and 2.4 times respectively compared with that of the wild phytase, in the benefit of the development of economical feed enzyme industry.

EMBODIMENT

The present invention is further illustrated with reference to the following Examples and the appended drawings, which should by no means be construed as limitations of the present invention.

Test Materials and Reagents

1. Strains and vectors: Expression vector pET-22b (+) and host strain BL21 (DE3) (INovagen).
2. Enzymes and other biochemical reagents: restriction endonucleases (TaKaRa), ligase (Invitrogen), and pepsin (p0685).
3. Medium:

*E. coli.* LB medium: 1% of peptone, 0.5% of yeast extract, and 1% of NaCl, natural pH.

Suitable biology laboratory methods not particularly mentioned in the examples as below can be found in Sambrook, et al. (*Molecular Cloning: A Laboratory Manual. 2nd, ed, Cold Spring Harbor Laboratory*, Cold Spring Harbor Laboratory Press, Cold Spring Harbor, N.Y., 1989), and other kit laboratory manuals.

Example 1 Introduction of the Mutant Site to Wild Phytase

Gene encoding phytase YeAPPA having the nucleotide sequence as set in SEQ ID NO. 2 was performed with site-directed mutagenesis by Overlap PCR to obtain the genes enconding phytase variants YeAPPA-L162G, YeAPPA-L162A, YeAPPA-E230G, YeAPPA-E230P and YeAPPA-E230R, respectively. Overlap PCR was performed as being kept at 95° C. for 5 min, followed by 30 cycles of 94° C. for 30 sec, 55° C. for 30 sec, and 72° C. for 30-90 sec, and keep 72° C. for 10 min, with 12 mutation primers including the upper primer Ye-F and the reverse primer Ye-R for amplifying the foil length of mutant gene, and the primers comprising the EcoRI and NotI sites marked in Italics or the mutant nucleotides marked in underlined for site-directed mutagenesis showed as below.

```
Ye-F/SEQ. ID. No. 13:
5'-cgcgaattcgccccgattgctacaccgcc-3'

Ye-R/SEQ. ID. No. 14:
5'-gatgcggccgcttaaatatggcaggctggctcga-3'

L162G-F/SEQ. ID. No. 15:
5'-cgggggtctgtaaaggcgactcagcgaaaac-3'

L162G-R/SEQ. ID. No. 16:
5'-gttttcgctgagtcgcctttacagacccccg-3'

L162A-F/SEQ. ID. No. 17:
5'-cgggggtctgtaaagcggactcagcgaaaac-3'

L162A-R/SEQ. ID. No. 18:
5'-gttttcgctgagtccgctttacagacccccg-3'

E230G-F/SEQ. ID. No. 19:
5'-ttaaggtaaacgaaggcggtactaaagtttc-3'

E230G-R/SEQ. ID. No. 20:
5'-gaaactttagtaccgccttcgtttaccttaa-3'

E230P-F/SEQ. ID. No. 21:
5'-ttaaggtaaacgaaccgggtactaaagtttc-3'

E230P-R/SEQ. ID. No. 22:
5'-gaaactttagtacccggttcgtttaccttaa-3'

E230R-F/SEQ. ID. No. 23:
5'-ttaaggtaaacgaacgtggtactaaagtttc-3'

E230R-R/SEQ. ID. No. 24:
5'-gaaactttagtaccacgttcgtttaccttaa-3'
```

The modified gene is recovered, connected with the vector pEASY-T3, and sequenced.

Example 2 Preparing the Phytase Variants and Measuring their Activity

The modified gene encoding the phytase variants were inserted into expression vector pET-22b (+), and transformed into *E coli*. Strain BL21 (DE3), which was induced by IPTG in 1 mM, cultivated for 5 h at 24° C. to express the phytase, followed by being purified by columns Ni-NTA and DEAE to obtain the mutant protein with the same molecular weight as that of the wild.

Example 3 Measuring Effect of Pepsin on the Enzyme Activity of the Phytase Variants Pepsin resistance of the phytase variants was measured by the remained activity and the amount of protein after being treated with different concentrations of pepsin.

Determining Effect of Pepsin on Activity of the Phytase Variants

Figure 1:
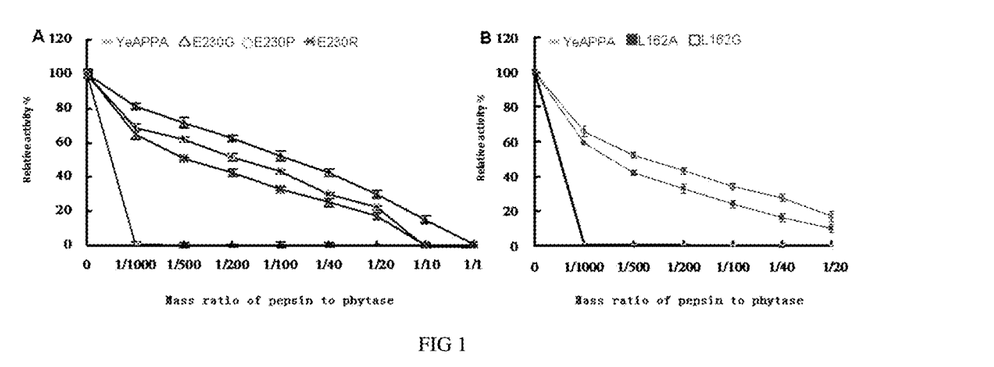
FIG. 1 shows the comparison of effect of pepsin on activity of the modified phytase and the wild phytase.

The effect of pepsin on the activity of the purified mutant phytase was determined by detecting the remained activity after being treated in pH 2 for 2 hours with the different concentrations of pepsin in a mass ratio to phytase ranging from 1/1000 to 1/1. The activity of phytase was detected by ferric molybdenum sulfate blue method by adding 50 ul of phytase solution to 950 ul of sodium phytate substrate in 1.5 mmol/L to react for 30 min at 37° C., followed by adding 1 mL of 10% (m/v) TCA to stop the reaction, and 2 mL of developing color reagent. After developing, OD is measured at 700 nm to calculate the phytase activity. 1 unit of phytase activity is determined to be the enzyme amount releasing 1 μmol of phosphate for 1 minute. The absolute value of the measured phytase activity may be calculated based on the standard curve of inorganic phosphate in dilution. As showed by "A" and "B" of FIG. 1, the phytase variants remained more enzyme activity after being treated for 2 h with different concentration of pepsin, than that of the wild phytase, wherein the retained activity of the phytase variants YeAPPA-E230G, YeAPPA-E230P, YeAPPA-E230R, YeAPPA-L162G and YeAPPA-L162A were 30%, 22%, 17%, 17% and 10% in order, but the wild phytase almost lost activity, demonstrating that pepsin resistance of phytase variants were improved.

Determining Effect of Pepsin on Stability of the Phytase Variants

Figure 2:
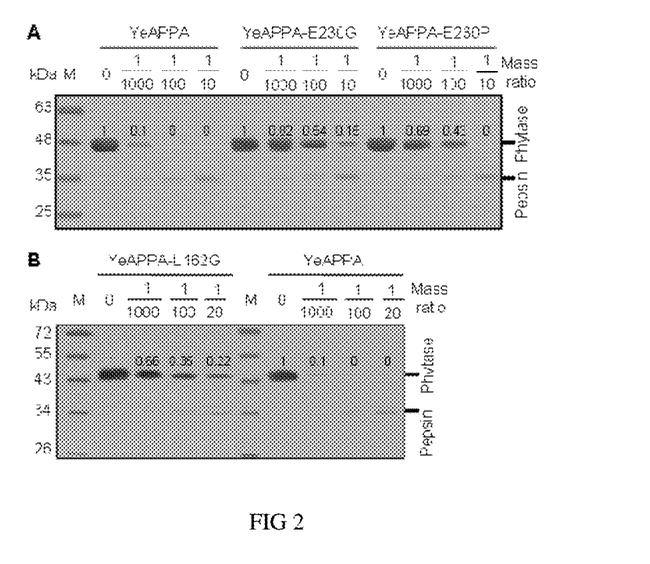
FIG. 2 shows the comparison of the acid resistance of the modified phytase and the wild phytase.

The effect of pepsin on the activity of the purified phytase variants was determined by detecting the retained phytase proteins by PAGE after being treated in pH 2 for 2 hours with the different concentrations of pepsin, and calculating the gray value of phytase protein bands. The amount of the retained phytase proteins after being treated with pepsin was represented by the ratio of the gray value of the retained phytase protein bands to that of the untreated, phytase bands. As showed in "A" and "B" of FIG. 2, the amounts of the retained protein of the phytase variants YeAPPA-E230G, YeAPPA-E230P, YeAPPA-E230R, YeAPPA-L162G and YeAPPA-L162A were more than that of the wild phytase with the ratio of 0.1, in case of being treated by pepsin in a ratio of 1/1000, and, the ratios of the gray value for the phytase variants YeAPPA-E230G, YeAPPA-E230P, YeAPPA-E230R, YeAPPA-L162G and YeAPPA-L162A were 0.54, 0.43, 0.33, 0.35, 0.25 in order, in case of being treated by pepsin in a ratio of 1/100. Therefore, the phytase variants of the present invention showed more retaining protein than that of the wild phytase after being treated with the different concentrations of pepsin, demonstrating that the phytase variants had the improve stability compare with the wild phytase.

Example 4 Determining Stability of the Phytase Variants (1) pH Stability

The purified phytase variant was performed the enzymatic reactions in the substrate solutions with, the different pHs using 0.1 mol/L of Glycine-HCl buffer (pH1.0~3.0), 0.1 mol/L of acetic acid-sodium acetate buffer (pH3~6), 0.1 mol/L of Tris-Hcl buffer (pH6~8) and 0.1 mol/L of glycine-sodium hydroxide buffer (pH8~12.0) at 37° C. to determine the optimal pH. As showed in Table 1, the optimal pH values of the phytase variants YeAPPA-E230G, YeAPPA-E230P, YeAPPA-L162G and YeAPPA-L162A were pH 5.0 being similar to that of the wild enzyme, other than the phytase variant YeAPPA-E230R decreased one pH unit in optimal pH value. And, the phytase variants YeAPPA-E230G, YeAPPA-E230P, YeAPPA-E230R, YeAPPA-L162G and YeAPPA-L162A retaining more than 18-32% of enzyme activity were more stable than the wild phytase retaining 12% of enzyme activity after being treated in pH 1.0 to 2.0 for 1 hour.

(2) Thermostability

The purified phytase variants were kept for 30 min at 30° C. to 80° C., respectively to determine their optimal temperatures. As list in Table 1, the optimal temperatures of the phytase variant YeAPPA-E230P was 50° C., which was 5° C. higher than those of the phytase variants YeAPPA-L162G, YeAPPA-L162A, YeAPPA-E230G, and YeAPPA-E230/R. And, phytase variants YeAPPA-E230P, YeAPPA-E230G and YeAPPA-E230R retaining 12%, 21% and 9% of enzyme activity were more thermostable than phytase variants YeAPPA-L162G, YeAPPA-L162A and the wild phytase losing all of enzyme activity after being kept for 30 min at 60° C. Therefore, phytase variants YeAPPA-E230P, YeAPPA-E230G and YeAPPA-E230R were more thermostable than the wild phytase.

TABLE 1

Comparison of the effect temperature and pH on the activity and stability of the modified phytase and the wild phytase

| Variants | Optimal pH | Optimal temperature | pH stability of the phytase after being treated in different pHs | Thermostability of phytase kept for 30 min at 60° C. |
|---|---|---|---|---|
| YeAPPA | 5 | 45° C. | pH 1-2, <12, pH 3-9, >89 | 0.6% |
| YeAPPA-L162G | 5 | 45° C. | pH 1-2, >20, pH 3-9, >99 | 0.6% |
| YeAPPA-L162A | 5 | 45° C. | pH 1-2, >18, pH 3-9, >96 | 0.6% |
| YeAPPA-E230G | 5 | 45° C. | pH 1-2, >32, pH 3-9, >100 | 21% |
| YeAPPA-E230P | 5 | 50° C. | pH 1-2, >24, pH 3-9, >99 | 12% |
| YeAPPA-E230R | 4 | 45° C. | pH 1-2, >30, pH 3-9, >99 | 9% |

Example 5 Measuring Kinetic Parameter of the Phytase Variants

The activity of phytase was measured with sodium phytate as substrate in different concentrations of 0.0625 mmol/L, 0.1 mmol/L, 0.125 mmol/L, 0.2 mmol/L, 0.25 mmol/L, 0.5 mmol/L, 1.0 mmol/L and 1.5 mmol/L at the optimal temperature and pH, followed by calculating the values of $k_m$ and $V_{max}$ double reciprocal method for Michaelis equation, and $K_{cat}$ according to the theoretical molecular weight. As showed in Table 2, the affinity to substrate ($k_m$) of each of phytase variants was similar to that of the wild phytase. Reaction rate $V_{max}$ and conversion rate $K_{cat}$ of the phytase variant YeAPPA-E230G were greatly increased to 2.5 times of that of the wild phytase, and catalytic efficiency $K_{cat}/k_m$ was 2.5 times of that of the wild phytase. Reaction rate $V_{max}$ and conversion rate $K_{cat}$ of the phytase variant YeAPPA-L162G were increased to 1.6 to 1.8 times of that of the wild phytase, and catalytic efficiency $K_{cat}/k_m$ was 1.7 times of that of the wild phytase. And, reaction rate, conversion rate and catalytic efficiency of the phytase variants YeAPPA-L162A, YeAPPA-E230P and YeAPPA-E230R were almost same as those of the wild phytase.

TABLE 2

Comparison of the enzymatic properties of
the modified phytase and the wild phytase

| Phytase | Km(mM) | Vmax(U mg$^{-1}$) | Kcat(S$^{-1}$) | Kcat/Km(S$^{-1}$ mM$^{-1}$) |
|---|---|---|---|---|
| YeAPPA | 0.19 | 6.4 | 4.9 | 26 |
| YeAPPA-L162G | 0.19 | 11 | 8.2 | 43 |
| YeAPPA-L162A | 0.19 | 6.5 | 5.0 | 27 |
| YeAPPA-E230G | 0.19 | 16 | 12 | 64 |
| YeAPPA-E230P | 0.19 | 6.7 | 5.1 | 26 |
| YeAPPA-E230R | 0.18 | 6.3 | 4.8 | 26 |

The invention claimed is:

1. A phytase variant having phytase activity and comprising the amino acid sequence of SEQ ID NO: 1, except the glutamate corresponding to position 230 of SEQ ID NO: 1 is replaced with glycine, proline or arginine, and wherein the phytase variant has improved pepsin resistance and acid resistance, and increased catalytic efficiency as compared to a phytase consisting of the amino acid sequence of SEQ ID NO: 1.

2. A polynucleotide comprising a nucleotide sequence encoding the phytase variant of claim 1.

3. The polynucleotide according to claim 2, wherein said polynucleotide comprises the nucleotide sequence of SEQ ID NO: 10, SEQ ID NO: 11, or SEQ ID NO: 12.

4. A DNA construct comprising the polynucleotide of claim 2.

5. An isolated recombinant cell comprising the polynucleotide of claim 2.

6. A method of producing the phytase variant of claim 1, comprising the steps of transforming an isolated host cell with a DNA construct comprising a polynucleotide which comprises a nucleotide sequence encoding said phytase variant to obtain a recombinant host cell; cultivating the recombinant host cell to produce the phytase variant; and recovering the phytase variant.

* * * * *

SEQUENCE LISTING

<160> NUMBER OF SEQ ID NOS: 24

<210> SEQ ID NO 1
<211> LENGTH: 441
<212> TYPE: PRT
<213> ORGANISM: Yersinia enterocolitica

<400> SEQUENCE: 1

```
Met Ser Val Ala Lys Arg Asn Leu His Leu Ser Ala Leu Thr Leu Ile
1               5                   10                  15

Met Gly Cys Phe Thr Ala Gly Ala Ala Pro Ile Ala Thr Pro Pro Ala
            20                  25                  30

Ser Tyr Thr Leu Glu Arg Val Val Ile Leu Ser Arg His Gly Val Arg
        35                  40                  45

Ser Pro Thr Lys Gln Thr Gln Leu Met Asn Asp Val Thr Pro Asp Lys
    50                  55                  60

Trp Pro Leu Trp Pro Val Lys Ala Gly Tyr Leu Thr Pro Arg Arg Ala
65                  70                  75                  80

Glu Leu Val Thr Leu Met Gly Gly Phe Tyr Gly Asp Tyr Phe Arg Ser
                85                  90                  95

Gln Gly Leu Leu Ser Ala Gly Cys Pro Val Asp Gly Ser Val Tyr Ala
            100                 105                 110

Gln Ala Asp Val Asp Gln Arg Thr Arg Leu Thr Gly Gln Ala Phe Leu
        115                 120                 125

Asp Gly Ile Ala Pro Asp Cys Gly Leu Lys Val His Tyr Gln Ala Asp
    130                 135                 140

Leu Lys Lys Val Asp Pro Leu Phe His Thr Val Glu Ala Gly Val Cys
145                 150                 155                 160

Lys Leu Asp Ser Ala Lys Thr His Gln Ala Val Glu Glu Arg Leu Gly
                165                 170                 175

Gly Pro Leu Ser Asp Leu Ser Gln Arg Tyr Ala Lys Pro Phe Ala Gln
            180                 185                 190

Met Gly Glu Val Leu Asn Phe Ala Ala Ser Pro Tyr Cys Lys Ser Leu
        195                 200                 205

Gln Lys Asn Gly Lys Thr Cys Asp Phe Ala Thr Phe Thr Ala Asn Glu
    210                 215                 220

Ile Lys Val Asn Glu Glu Gly Thr Lys Val Ser Leu Ser Gly Pro Leu
225                 230                 235                 240

Ala Leu Ser Ser Thr Leu Gly Glu Ile Phe Leu Leu Gln Asp Ser Gln
                245                 250                 255

Ala Met Pro Asp Val Ala Trp His Arg Leu Ser Gly Glu Glu Asn Trp
            260                 265                 270

Val Ser Leu Leu Ser Leu Arg Asn Ala Gln Phe Asp Leu Met Ala Lys
```

```
            275                 280                 285
Thr Pro Tyr Ile Ala Arg His Lys Gly Thr Pro Leu Leu Gln Gln Ile
    290                 295                 300

Asp Thr Ala Leu Val Leu Gln Arg Asp Ala Gln Gly Gln Thr Leu Pro
305                 310                 315                 320

Leu Ser Pro Gln Thr Lys Leu Leu Phe Leu Gly Gly His Asp Thr Asn
                325                 330                 335

Ile Ala Asn Ile Ala Gly Met Leu Gly Ala Asn Trp Gln Leu Pro Gln
                340                 345                 350

Gln Pro Asp Asn Thr Pro Pro Gly Gly Gly Leu Val Phe Glu Leu Trp
            355                 360                 365

Gln Asn Pro Asp Asn His Gln Arg Tyr Val Ala Val Lys Met Phe Tyr
    370                 375                 380

Gln Thr Met Asp Gln Leu Arg Asn Ala Glu Lys Leu Asp Met Lys Asn
385                 390                 395                 400

Asn Pro Ala Lys Ile Val Pro Ile Thr Ile Glu Gly Cys Glu Asn Glu
                405                 410                 415

Gly Asp Asn Lys Leu Cys Gln Leu Glu Thr Phe Gln Lys Lys Val Ala
                420                 425                 430

Gln Val Ile Glu Pro Ala Cys His Ile
                435                 440

<210> SEQ ID NO 2
<211> LENGTH: 1326
<212> TYPE: DNA
<213> ORGANISM: Yersinia enterocolitica

<400> SEQUENCE: 2
atgtcagttg caaagagaaa tctgcactta tccgcactca ctttgataat gggctgtttt      60
accgcaggtg ctgccccgat tgctacaccg ccggccagct acacattaga gcgtgtggtt     120
attttgagtc gacatggtgt tcgctccccg acaaaacaaa cccagctaat gaatgatgtc     180
acacctgata aatggcccct gtggccagta aaagcgggct atttaacacc gcgaagggct     240
gagttagtga ctttgatggg gggattttat ggtgattatt tccgcagcca agggttgttg     300
tctgcggggt gtccggtaga tggctccgtt tatgcacagg cagatgttga ccaacgaacc     360
cgcttaaccg gacaggcatt cttggatggg atcgcaccgg attgtggtct gaaagtacat     420
tatcaggctg atttgaagaa agttgacccg ctatttcata ccgtcgaagc gggggtctgt     480
aaactggact cagcgaaaac tcatcaggct gttgaggagc gattgggcgg gccattgagt     540
gatcttagcc agcgctatgc caaacccttt gctcagatgg gcgaagtgct gaattttgca     600
gcatcgcctt attgcaagtc attgcaaaaa aatggaaaaa cctgtgattt tgcaactttt     660
acggcaaatg aaattaaggt aaacgaagaa ggtactaaag tttctctgag tgggccattg     720
gcactatcgt cgacattggg tgaaattttc ctgttacaag actcacaagc tatgccggat     780
gtggcctggc atcggctcag cggtgaagag aactgggttt cgctattgtc gttgcgcaat     840
gcgcaatttg atttgatggc caaaaccccg tatatcgctc gccataaagg gaccccgctg     900
ttgcaacaaa ttgatacggc attagtgctg caacgcgatg cccaagggca aacactgccg     960
ctgtcaccgc aaaccaaatt gctgttcctc ggcgggcatg acaccaatat tgctaatatc    1020
gctggtatgt taggggccaa ttggcaatta ccacagcaac ctgataatac cccgcctggt    1080
ggcggattag tctttgagct atggcagaac ccagataatc atcagcgcta tgtcgccgtg    1140
aaaatgttct atcaaacgat ggatcagctg cgaaatgccg agaaattaga tatgaaaaac    1200
```

-continued

```
aacccagcta aaattgttcc aattaccatt gaaggttgtg agaacgaggg tgataacaaa    1260
ctttgccaac ttgagacttt ccaaaagaaa gttgcccaag tgatcgagcc agcctgccat    1320
atttaa                                                                1326
```

<210> SEQ ID NO 3
<211> LENGTH: 441
<212> TYPE: PRT
<213> ORGANISM: Artificial Sequence
<220> FEATURE:
<223> OTHER INFORMATION: VARIANT

<400> SEQUENCE: 3

```
Met Ser Val Ala Lys Arg Asn Leu His Leu Ser Ala Leu Thr Leu Ile
1               5                   10                  15

Met Gly Cys Phe Thr Ala Gly Ala Ala Pro Ile Ala Thr Pro Pro Ala
            20                  25                  30

Ser Tyr Thr Leu Glu Arg Val Val Ile Leu Ser Arg His Gly Val Arg
        35                  40                  45

Ser Pro Thr Lys Gln Thr Gln Leu Met Asn Asp Val Thr Pro Asp Lys
    50                  55                  60

Trp Pro Leu Trp Pro Val Lys Ala Gly Tyr Leu Thr Pro Arg Arg Ala
65                  70                  75                  80

Glu Leu Val Thr Leu Met Gly Gly Phe Tyr Gly Asp Tyr Phe Arg Ser
                85                  90                  95

Gln Gly Leu Leu Ser Ala Gly Cys Pro Val Asp Gly Ser Val Tyr Ala
            100                 105                 110

Gln Ala Asp Val Asp Gln Arg Thr Arg Leu Thr Gly Gln Ala Phe Leu
        115                 120                 125

Asp Gly Ile Ala Pro Asp Cys Gly Leu Lys Val His Tyr Gln Ala Asp
    130                 135                 140

Leu Lys Lys Val Asp Pro Leu Phe His Thr Val Glu Ala Gly Val Cys
145                 150                 155                 160

Lys Gly Asp Ser Ala Lys Thr His Gln Ala Val Glu Glu Arg Leu Gly
                165                 170                 175

Gly Pro Leu Ser Asp Leu Ser Gln Arg Tyr Ala Lys Pro Phe Ala Gln
            180                 185                 190

Met Gly Glu Val Leu Asn Phe Ala Ala Ser Pro Tyr Cys Lys Ser Leu
        195                 200                 205

Gln Lys Asn Gly Lys Thr Cys Asp Phe Ala Thr Phe Thr Ala Asn Glu
    210                 215                 220

Ile Lys Val Asn Glu Glu Gly Thr Lys Val Ser Leu Ser Gly Pro Leu
225                 230                 235                 240

Ala Leu Ser Ser Thr Leu Gly Glu Ile Phe Leu Leu Gln Asp Ser Gln
                245                 250                 255

Ala Met Pro Asp Val Ala Trp His Arg Leu Ser Gly Glu Glu Asn Trp
            260                 265                 270

Val Ser Leu Leu Ser Leu Arg Asn Ala Gln Phe Asp Leu Met Ala Lys
        275                 280                 285

Thr Pro Tyr Ile Ala Arg His Lys Gly Thr Pro Leu Leu Gln Gln Ile
    290                 295                 300

Asp Thr Ala Leu Val Leu Gln Arg Asp Ala Gln Gly Gln Thr Leu Pro
305                 310                 315                 320

Leu Ser Pro Gln Thr Lys Leu Leu Phe Leu Gly Gly His Asp Thr Asn
                325                 330                 335
```

```
Ile Ala Asn Ile Ala Gly Met Leu Gly Ala Asn Trp Gln Leu Pro Gln
                340             345                 350

Gln Pro Asp Asn Thr Pro Pro Gly Gly Leu Val Phe Glu Leu Trp
            355             360             365

Gln Asn Pro Asp Asn His Gln Arg Tyr Val Ala Val Lys Met Phe Tyr
        370             375             380

Gln Thr Met Asp Gln Leu Arg Asn Ala Glu Lys Leu Asp Met Lys Asn
385             390             395                 400

Asn Pro Ala Lys Ile Val Pro Ile Thr Ile Glu Gly Cys Glu Asn Glu
                405             410             415

Gly Asp Asn Lys Leu Cys Gln Leu Glu Thr Phe Gln Lys Val Ala
            420             425             430

Gln Val Ile Glu Pro Ala Cys His Ile
            435             440

<210> SEQ ID NO 4
<211> LENGTH: 441
<212> TYPE: PRT
<213> ORGANISM: Artificial Sequence
<220> FEATURE:
<223> OTHER INFORMATION: VARIANT

<400> SEQUENCE: 4

Met Ser Val Ala Lys Arg Asn Leu His Leu Ser Ala Leu Thr Leu Ile
1               5                   10                  15

Met Gly Cys Phe Thr Ala Gly Ala Ala Pro Ile Ala Thr Pro Pro Ala
                20                  25                  30

Ser Tyr Thr Leu Glu Arg Val Val Ile Leu Ser Arg His Gly Val Arg
            35                  40                  45

Ser Pro Thr Lys Gln Thr Gln Leu Met Asn Asp Val Thr Pro Asp Lys
        50                  55                  60

Trp Pro Leu Trp Pro Val Lys Ala Gly Tyr Leu Thr Pro Arg Arg Ala
65                  70                  75                  80

Glu Leu Val Thr Leu Met Gly Gly Phe Tyr Gly Asp Tyr Phe Arg Ser
                85                  90                  95

Gln Gly Leu Leu Ser Ala Gly Cys Pro Val Asp Gly Ser Val Tyr Ala
            100                 105                 110

Gln Ala Asp Val Asp Gln Arg Thr Arg Leu Thr Gly Gln Ala Phe Leu
        115                 120                 125

Asp Gly Ile Ala Pro Asp Cys Gly Leu Lys Val His Tyr Gln Ala Asp
    130                 135                 140

Leu Lys Lys Val Asp Pro Leu Phe His Thr Val Glu Ala Gly Val Cys
145                 150                 155                 160

Lys Ala Asp Ser Ala Lys Thr His Gln Ala Val Glu Glu Arg Leu Gly
                165                 170                 175

Gly Pro Leu Ser Asp Leu Ser Gln Arg Tyr Ala Lys Pro Phe Ala Gln
            180                 185                 190

Met Gly Glu Val Leu Asn Phe Ala Ala Ser Pro Tyr Cys Lys Ser Leu
        195                 200                 205

Gln Lys Asn Gly Lys Thr Cys Asp Phe Ala Thr Phe Thr Ala Asn Glu
    210                 215                 220

Ile Lys Val Asn Glu Glu Gly Thr Lys Val Ser Leu Ser Gly Pro Leu
225                 230                 235                 240

Ala Leu Ser Ser Thr Leu Gly Glu Ile Phe Leu Leu Gln Asp Ser Gln
                245                 250                 255
```

```
Ala Met Pro Asp Val Ala Trp His Arg Leu Ser Gly Glu Glu Asn Trp
            260                 265                 270

Val Ser Leu Leu Ser Leu Arg Asn Ala Gln Phe Asp Leu Met Ala Lys
            275                 280                 285

Thr Pro Tyr Ile Ala Arg His Lys Gly Thr Pro Leu Leu Gln Gln Ile
            290                 295                 300

Asp Thr Ala Leu Val Leu Gln Arg Asp Ala Gln Gly Gln Thr Leu Pro
305                 310                 315                 320

Leu Ser Pro Gln Thr Lys Leu Leu Phe Leu Gly Gly His Asp Thr Asn
                325                 330                 335

Ile Ala Asn Ile Ala Gly Met Leu Gly Ala Asn Trp Gln Leu Pro Gln
                340                 345                 350

Gln Pro Asp Asn Thr Pro Pro Gly Gly Gly Leu Val Phe Glu Leu Trp
            355                 360                 365

Gln Asn Pro Asp Asn His Gln Arg Tyr Val Ala Val Lys Met Phe Tyr
            370                 375                 380

Gln Thr Met Asp Gln Leu Arg Asn Ala Glu Lys Leu Asp Met Lys Asn
385                 390                 395                 400

Asn Pro Ala Lys Ile Val Pro Ile Thr Ile Glu Gly Cys Glu Asn Glu
                405                 410                 415

Gly Asp Asn Lys Leu Cys Gln Leu Glu Thr Phe Gln Lys Lys Val Ala
                420                 425                 430

Gln Val Ile Glu Pro Ala Cys His Ile
            435                 440

<210> SEQ ID NO 5
<211> LENGTH: 441
<212> TYPE: PRT
<213> ORGANISM: Artificial Sequence
<220> FEATURE:
<223> OTHER INFORMATION: VARIANT

<400> SEQUENCE: 5

Met Ser Val Ala Lys Arg Asn Leu His Leu Ser Ala Leu Thr Leu Ile
1               5                   10                  15

Met Gly Cys Phe Thr Ala Gly Ala Ala Pro Ile Ala Thr Pro Pro Ala
                20                  25                  30

Ser Tyr Thr Leu Glu Arg Val Val Ile Leu Ser Arg His Gly Val Arg
            35                  40                  45

Ser Pro Thr Lys Gln Thr Gln Leu Met Asn Asp Val Thr Pro Asp Lys
    50                  55                  60

Trp Pro Leu Trp Pro Val Lys Ala Gly Tyr Leu Thr Pro Arg Arg Ala
65                  70                  75                  80

Glu Leu Val Thr Leu Met Gly Gly Phe Tyr Gly Asp Tyr Phe Arg Ser
                85                  90                  95

Gln Gly Leu Leu Ser Ala Gly Cys Pro Val Asp Gly Ser Val Tyr Ala
            100                 105                 110

Gln Ala Asp Val Asp Gln Arg Thr Arg Leu Thr Gly Gln Ala Phe Leu
        115                 120                 125

Asp Gly Ile Ala Pro Asp Cys Gly Leu Lys Val His Tyr Gln Ala Asp
        130                 135                 140

Leu Lys Lys Val Asp Pro Leu Phe His Thr Val Glu Ala Gly Val Cys
145                 150                 155                 160

Lys Leu Asp Ser Ala Lys Thr His Gln Ala Val Glu Glu Arg Leu Gly
                165                 170                 175
```

Gly Pro Leu Ser Asp Leu Ser Gln Arg Tyr Ala Lys Pro Phe Ala Gln
            180                 185                 190

Met Gly Glu Val Leu Asn Phe Ala Ala Ser Pro Tyr Cys Lys Ser Leu
        195                 200                 205

Gln Lys Asn Gly Lys Thr Cys Asp Phe Ala Thr Phe Thr Ala Asn Glu
    210                 215                 220

Ile Lys Val Asn Glu Gly Gly Thr Lys Val Ser Leu Ser Gly Pro Leu
225                 230                 235                 240

Ala Leu Ser Ser Thr Leu Gly Glu Ile Phe Leu Leu Gln Asp Ser Gln
                245                 250                 255

Ala Met Pro Asp Val Ala Trp His Arg Leu Ser Gly Glu Glu Asn Trp
            260                 265                 270

Val Ser Leu Leu Ser Leu Arg Asn Ala Gln Phe Asp Leu Met Ala Lys
        275                 280                 285

Thr Pro Tyr Ile Ala Arg His Lys Gly Thr Pro Leu Leu Gln Gln Ile
    290                 295                 300

Asp Thr Ala Leu Val Leu Gln Arg Asp Ala Gln Gly Gln Thr Leu Pro
305                 310                 315                 320

Leu Ser Pro Gln Thr Lys Leu Leu Phe Leu Gly Gly His Asp Thr Asn
                325                 330                 335

Ile Ala Asn Ile Ala Gly Met Leu Gly Ala Asn Trp Gln Leu Pro Gln
            340                 345                 350

Gln Pro Asp Asn Thr Pro Pro Gly Gly Gly Leu Val Phe Glu Leu Trp
        355                 360                 365

Gln Asn Pro Asp Asn His Gln Arg Tyr Val Ala Val Lys Met Phe Tyr
    370                 375                 380

Gln Thr Met Asp Gln Leu Arg Asn Ala Glu Lys Leu Asp Met Lys Asn
385                 390                 395                 400

Asn Pro Ala Lys Ile Val Pro Ile Thr Ile Glu Gly Cys Glu Asn Glu
                405                 410                 415

Gly Asp Asn Lys Leu Cys Gln Leu Glu Thr Phe Gln Lys Lys Val Ala
            420                 425                 430

Gln Val Ile Glu Pro Ala Cys His Ile
        435                 440

<210> SEQ ID NO 6
<211> LENGTH: 441
<212> TYPE: PRT
<213> ORGANISM: Artificial Sequence
<220> FEATURE:
<223> OTHER INFORMATION: VARIANT

<400> SEQUENCE: 6

Met Ser Val Ala Lys Arg Asn Leu His Leu Ser Ala Leu Thr Leu Ile
1               5                   10                  15

Met Gly Cys Phe Thr Ala Gly Ala Ala Pro Ile Ala Thr Pro Pro Ala
            20                  25                  30

Ser Tyr Thr Leu Glu Arg Val Val Ile Leu Ser Arg His Gly Val Arg
        35                  40                  45

Ser Pro Thr Lys Gln Thr Gln Leu Met Asn Asp Val Thr Pro Asp Lys
    50                  55                  60

Trp Pro Leu Trp Pro Val Lys Ala Gly Tyr Leu Thr Pro Arg Arg Ala
65                  70                  75                  80

Glu Leu Val Thr Leu Met Gly Gly Phe Tyr Gly Asp Tyr Phe Arg Ser
                85                  90                  95

Gln Gly Leu Leu Ser Ala Gly Cys Pro Val Asp Gly Ser Val Tyr Ala
            100                 105                 110

Gln Ala Asp Val Asp Gln Arg Thr Arg Leu Thr Gly Gln Ala Phe Leu
        115                 120                 125

Asp Gly Ile Ala Pro Asp Cys Gly Leu Lys Val His Tyr Gln Ala Asp
    130                 135                 140

Leu Lys Lys Val Asp Pro Leu Phe His Thr Val Glu Ala Gly Val Cys
145                 150                 155                 160

Lys Leu Asp Ser Ala Lys Thr His Gln Ala Val Glu Arg Leu Gly
                165                 170                 175

Gly Pro Leu Ser Asp Leu Ser Gln Arg Tyr Ala Lys Pro Phe Ala Gln
                180                 185                 190

Met Gly Glu Val Leu Asn Phe Ala Ala Ser Pro Tyr Cys Lys Ser Leu
            195                 200                 205

Gln Lys Asn Gly Lys Thr Cys Asp Phe Ala Thr Phe Thr Ala Asn Glu
        210                 215                 220

Ile Lys Val Asn Glu Pro Gly Thr Lys Val Ser Leu Ser Gly Pro Leu
225                 230                 235                 240

Ala Leu Ser Ser Thr Leu Gly Glu Ile Phe Leu Leu Gln Asp Ser Gln
                245                 250                 255

Ala Met Pro Asp Val Ala Trp His Arg Leu Ser Gly Glu Glu Asn Trp
            260                 265                 270

Val Ser Leu Leu Ser Leu Arg Asn Ala Gln Phe Asp Leu Met Ala Lys
        275                 280                 285

Thr Pro Tyr Ile Ala Arg His Lys Gly Thr Pro Leu Leu Gln Gln Ile
    290                 295                 300

Asp Thr Ala Leu Val Leu Gln Arg Asp Ala Gln Gly Gln Thr Leu Pro
305                 310                 315                 320

Leu Ser Pro Gln Thr Lys Leu Leu Phe Leu Gly Gly His Asp Thr Asn
                325                 330                 335

Ile Ala Asn Ile Ala Gly Met Leu Gly Ala Asn Trp Gln Leu Pro Gln
            340                 345                 350

Gln Pro Asp Asn Thr Pro Pro Gly Gly Leu Val Phe Glu Leu Trp
        355                 360                 365

Gln Asn Pro Asp Asn His Gln Arg Tyr Val Ala Val Lys Met Phe Tyr
    370                 375                 380

Gln Thr Met Asp Gln Leu Arg Asn Ala Glu Lys Leu Asp Met Lys Asn
385                 390                 395                 400

Asn Pro Ala Lys Ile Val Pro Ile Thr Ile Glu Gly Cys Glu Asn Glu
                405                 410                 415

Gly Asp Asn Lys Leu Cys Gln Leu Glu Thr Phe Gln Lys Lys Val Ala
            420                 425                 430

Gln Val Ile Glu Pro Ala Cys His Ile
        435                 440

<210> SEQ ID NO 7
<211> LENGTH: 441
<212> TYPE: PRT
<213> ORGANISM: Artificial Sequence
<220> FEATURE:
<223> OTHER INFORMATION: VARIANT

<400> SEQUENCE: 7

Met Ser Val Ala Lys Arg Asn Leu His Leu Ser Ala Leu Thr Leu Ile
1               5                   10                  15

```
Met Gly Cys Phe Thr Ala Gly Ala Ala Pro Ile Ala Thr Pro Pro Ala
            20                  25                  30

Ser Tyr Thr Leu Glu Arg Val Val Ile Leu Ser Arg His Gly Val Arg
            35                  40                  45

Ser Pro Thr Lys Gln Thr Gln Leu Met Asn Asp Val Thr Pro Asp Lys
 50                  55                  60

Trp Pro Leu Trp Pro Val Lys Ala Gly Tyr Leu Thr Pro Arg Arg Ala
 65                  70                  75                  80

Glu Leu Val Thr Leu Met Gly Gly Phe Tyr Gly Asp Tyr Phe Arg Ser
                85                  90                  95

Gln Gly Leu Leu Ser Ala Gly Cys Pro Val Asp Gly Ser Val Tyr Ala
            100                 105                 110

Gln Ala Asp Val Asp Gln Arg Thr Arg Leu Thr Gly Gln Ala Phe Leu
            115                 120                 125

Asp Gly Ile Ala Pro Asp Cys Gly Leu Lys Val His Tyr Gln Ala Asp
            130                 135                 140

Leu Lys Lys Val Asp Pro Leu Phe His Thr Val Glu Ala Gly Val Cys
145                 150                 155                 160

Lys Leu Asp Ser Ala Lys Thr His Gln Ala Val Glu Glu Arg Leu Gly
                165                 170                 175

Gly Pro Leu Ser Asp Leu Ser Gln Arg Tyr Ala Lys Pro Phe Ala Gln
            180                 185                 190

Met Gly Glu Val Leu Asn Phe Ala Ala Ser Pro Tyr Cys Lys Ser Leu
            195                 200                 205

Gln Lys Asn Gly Lys Thr Cys Asp Phe Ala Thr Phe Thr Ala Asn Glu
            210                 215                 220

Ile Lys Val Asn Glu Arg Gly Thr Lys Val Ser Leu Ser Gly Pro Leu
225                 230                 235                 240

Ala Leu Ser Ser Thr Leu Gly Glu Ile Phe Leu Leu Gln Asp Ser Gln
                245                 250                 255

Ala Met Pro Asp Val Ala Trp His Arg Leu Ser Gly Glu Glu Asn Trp
            260                 265                 270

Val Ser Leu Leu Ser Leu Arg Asn Ala Gln Phe Asp Leu Met Ala Lys
            275                 280                 285

Thr Pro Tyr Ile Ala Arg His Lys Gly Thr Pro Leu Leu Gln Gln Ile
            290                 295                 300

Asp Thr Ala Leu Val Leu Gln Arg Asp Ala Gln Gly Gln Thr Leu Pro
305                 310                 315                 320

Leu Ser Pro Gln Thr Lys Leu Leu Phe Leu Gly Gly His Asp Thr Asn
                325                 330                 335

Ile Ala Asn Ile Ala Gly Met Leu Gly Ala Asn Trp Gln Leu Pro Gln
            340                 345                 350

Gln Pro Asp Asn Thr Pro Pro Gly Gly Gly Leu Val Phe Glu Leu Trp
            355                 360                 365

Gln Asn Pro Asp Asn His Gln Arg Tyr Val Ala Val Lys Met Phe Tyr
            370                 375                 380

Gln Thr Met Asp Gln Leu Arg Asn Ala Glu Lys Leu Asp Met Lys Asn
385                 390                 395                 400

Asn Pro Ala Lys Ile Val Pro Ile Thr Ile Glu Gly Cys Glu Asn Glu
                405                 410                 415

Gly Asp Asn Lys Leu Cys Gln Leu Glu Thr Phe Gln Lys Lys Val Ala
            420                 425                 430
```

Gln Val Ile Glu Pro Ala Cys His Ile
        435                 440

<210> SEQ ID NO 8
<211> LENGTH: 1326
<212> TYPE: DNA
<213> ORGANISM: Artificial Sequence
<220> FEATURE:
<223> OTHER INFORMATION: VARIANT Gene

<400> SEQUENCE: 8

| | | | | | |
|---|---|---|---|---|---|
| atgtcagttg | caaagagaaa | tctgcactta | tccgcactca | ctttgataat | gggctgtttt | 60 |
| accgcaggtg | ctgccccgat | tgctacaccg | ccggccagct | acacattaga | gcgtgtggtt | 120 |
| attttgagtc | gacatggtgt | tcgctccccg | acaaaacaaa | cccagctaat | gaatgatgtc | 180 |
| acacctgata | aatggcccct | gtggccagta | aaagcgggct | atttaacacc | gcgaagggct | 240 |
| gagttagtga | ctttgatggg | gggatttttat | ggtgattatt | tccgcagcca | agggttgttg | 300 |
| tctgcggggt | gtccggtaga | tggctccgtt | tatgcacagg | cagatgttga | ccaacgaacc | 360 |
| cgcttaaccg | gacaggcatt | cttggatggg | atcgcaccgg | attgtggtct | gaaagtacat | 420 |
| tatcaggctg | atttgaagaa | agttgacccg | ctatttcata | ccgtcgaagc | ggggtctgt | 480 |
| aaaggcgact | cagcgaaaac | tcatcaggct | gttgaggagc | gattgggcgg | ccattgagt | 540 |
| gatcttagcc | agcgctatgc | caaacccttt | gctcagatgg | gcgaagtgct | gaattttgca | 600 |
| gcatcgcctt | attgcaagtc | attgcaaaaa | aatggaaaaa | cctgtgattt | tgcaactttt | 660 |
| acggcaaatg | aaattaaggt | aaacgaagaa | ggtactaaag | tttctctgag | tgggccattg | 720 |
| gcactatcgt | cgacattggg | tgaaatttc | ctgttacaag | actcacaagc | tatgccggat | 780 |
| gtggcctggc | atcggctcag | cggtgaagag | aactgggttt | cgctattgtc | gttgcgcaat | 840 |
| gcgcaatttg | atttgatggc | caaaaccccg | tatatcgctc | gccataaagg | gacccccgctg | 900 |
| ttgcaacaaa | ttgatacggc | attagtgctg | caacgcgatg | cccaagggca | aacactgccg | 960 |
| ctgtcaccgc | aaaccaaatt | gctgttcctc | ggcgggcatg | acaccaatat | tgctaatatc | 1020 |
| gctggtatgt | taggggccaa | ttggcaatta | ccacagcaac | ctgataatac | cccgcctggt | 1080 |
| ggcggattag | tctttgagct | atggcagaac | ccagataatc | atcagcgcta | tgtcgccgtg | 1140 |
| aaaatgttct | atcaaacgat | ggatcagctg | cgaaatgccg | agaaattaga | tatgaaaaac | 1200 |
| aacccagcta | aaattgttcc | aattaccatt | gaaggttgtg | agaacgaggg | tgataacaaa | 1260 |
| ctttgccaac | ttgagacttt | ccaaaagaaa | gttgcccaag | tgatcgagcc | agcctgccat | 1320 |
| atttaa | | | | | | 1326 |

<210> SEQ ID NO 9
<211> LENGTH: 1326
<212> TYPE: DNA
<213> ORGANISM: Artificial Sequence
<220> FEATURE:
<223> OTHER INFORMATION: VARIANT Gene

<400> SEQUENCE: 9

| | | | | | |
|---|---|---|---|---|---|
| atgtcagttg | caaagagaaa | tctgcactta | tccgcactca | ctttgataat | gggctgtttt | 60 |
| accgcaggtg | ctgccccgat | tgctacaccg | ccggccagct | acacattaga | gcgtgtggtt | 120 |
| attttgagtc | gacatggtgt | tcgctccccg | acaaaacaaa | cccagctaat | gaatgatgtc | 180 |
| acacctgata | aatggcccct | gtggccagta | aaagcgggct | atttaacacc | gcgaagggct | 240 |
| gagttagtga | ctttgatggg | gggatttttat | ggtgattatt | tccgcagcca | agggttgttg | 300 |

```
tctgcggggt gtccggtaga tggctccgtt tatgcacagg cagatgttga ccaacgaacc        360
cgcttaaccg gacaggcatt cttggatggg atcgcaccgg attgtggtct gaaagtacat        420
tatcaggctg atttgaagaa agttgacccg ctatttcata ccgtcgaagc ggggtctgt         480 aaagcggact cagcgaaaac tcatcaggct gttgaggagc gattgggcgg gccattgagt        540
gatcttagcc agcgctatgc caaacccttt gctcagatgg gcgaagtgct gaattttgca        600
gcatcgcctt attgcaagtc attgcaaaaa aatggaaaaa cctgtgattt tgcaactttt        660
acggcaaatg aaattaaggt aaacgaagaa ggtactaaag tttctctgag tgggccattg        720
gcactatcgt cgacattggg tgaaattttc ctgttacaag actcacaagc tatgccggat        780
gtggcctggc atcggctcag cggtgaagag aactgggttt cgctattgtc gttgcgcaat        840
gcgcaatttg atttgatggc caaaaccccg tatatcgctc gccataaagg accccgctg         900 ttgcaacaaa ttgatacggc attagtgctg caacgcgatg cccaagggca aacactgccg        960
ctgtcaccgc aaaccaaatt gctgttcctc ggcgggcatg acaccaatat tgctaatatc       1020
gctggtatgt tagggccaa ttggcaatta ccacagcaac tgataatac cccgcctggt         1080 ggcggattag tctttgagct atggcagaac ccagataatc atcagcgcta tgtcgccgtg       1140
aaaatgttct atcaaacgat ggatcagctg cgaaatgccg agaaattaga tatgaaaaac       1200
aacccagcta aaattgttcc aattaccatt gaaggttgtg agaacgaggg tgataacaaa       1260 cttttgccaac ttgagacttt ccaaaagaaa gttgcccaag tgatcgagcc agcctgccat     1320
atttaa                                                                  1326

<210> SEQ ID NO 10
<211> LENGTH: 1326
<212> TYPE: DNA
<213> ORGANISM: Artificial Sequence
<220> FEATURE:
<223> OTHER INFORMATION: VARIANT Gene

<400> SEQUENCE: 10
atgtcagttg caaagagaaa tctgcactta tccgcactca ctttgataat gggctgtttt        60
accgcaggtg ctgccccgat tgctacaccg ccggccagct acacattaga gcgtgtggtt       120
attttgagtc gacatggtgt tcgctccccg acaaaacaaa cccagctaat gaatgatgtc       180
acacctgata atggcccct gtggccagta aaagcgggct attaacacc gcgaagggct         240 gagttagtga ctttgatggg gggattttat ggtgattatt tccgcagcca agggttgttg       300
tctgcggggt gtccggtaga tggctccgtt tatgcacagg cagatgttga ccaacgaacc      360
cgcttaaccg gacaggcatt cttggatggg atcgcaccgg attgtggtct gaaagtacat      420
tatcaggctg atttgaagaa agttgacccg ctatttcata ccgtcgaagc ggggtctgt       480 aaactggact cagcgaaaac tcatcaggct gttgaggagc gattgggcgg gccattgagt      540
gatcttagcc agcgctatgc caaacccttt gctcagatgg gcgaagtgct gaattttgca      600
gcatcgcctt attgcaagtc attgcaaaaa aatggaaaaa cctgtgattt tgcaactttt      660
acggcaaatg aaattaaggt aaacgaaggc ggtactaaag tttctctgag tgggccattg      720
gcactatcgt cgacattggg tgaaattttc ctgttacaag actcacaagc tatgccggat      780
gtggcctggc atcggctcag cggtgaagag aactgggttt cgctattgtc gttgcgcaat      840
gcgcaatttg atttgatggc caaaaccccg tatatcgctc gccataaagg accccgctg       900 ttgcaacaaa ttgatacggc attagtgctg caacgcgatg cccaagggca aacactgccg      960
ctgtcaccgc aaaccaaatt gctgttcctc ggcgggcatg acaccaatat tgctaatatc    1020
```

```
gctggtatgt aggggccaa ttggcaatta ccacagcaac ctgataatac cccgcctggt    1080
ggcggattag tctttgagct atggcagaac ccagataatc atcagcgcta tgtcgccgtg    1140
aaaatgttct atcaaacgat ggatcagctg cgaaatgccg agaaattaga tatgaaaaac    1200
aacccagcta aaattgttcc aattaccatt gaaggttgtg agaacgaggg tgataacaaa    1260
ctttgccaac ttgagacttt ccaaaagaaa gttgcccaag tgatcgagcc agcctgccat    1320
atttaa                                                              1326

<210> SEQ ID NO 11
<211> LENGTH: 1326
<212> TYPE: DNA
<213> ORGANISM: Artificial Sequence
<220> FEATURE:
<223> OTHER INFORMATION: VARIANT Gene

<400> SEQUENCE: 11
atgtcagttg caaagagaaa tctgcactta tccgcactca ctttgataat gggctgtttt      60
accgcaggtg ctgccccgat tgctacaccg ccggccagct acacattaga gcgtgtggtt     120
attttgagtc gacatggtgt tcgctccccg acaaaacaaa cccagctaat gaatgatgtc     180
acacctgata aatggcccct gtggccagta aaagcgggct atttaacacc gcgaagggct     240
gagttagtga ctttgatggg gggatttta ggtgattatt tccgcagcca agggttgttg      300
tctgcggggt gtccggtaga tggctccgtt tatgcacagg cagatgttga ccaacgaacc     360
cgcttaaccg gacaggcatt cttggatggg atcgcaccgg attgtggtct gaaagtacat     420
tatcaggctg atttgaagaa agttgacccg ctatttcata ccgtcgaagc gggggtctgt     480
aaactggact cagcgaaaac tcatcaggct gttgaggagc gattgggcgg gccattgagt     540
gatcttagcc agcgctatgc caaacccttt gctcagatgg gcgaagtgct gaattttgca     600
gcatcgcctt attgcaagtc attgcaaaaa atggaaaaa cctgtgattt tgcaactttt      660
acggcaaatg aaattaaggt aaacgaaccg ggtactaaag tttctctgag tgggccattg     720
gcactatcgt cgacattggg tgaaattttc ctgttacaag actcacaagc tatgccggat     780
gtggcctggc atcggctcag cggtgaagag aactgggttt cgctattgtc gttgcgcaat     840
gcgcaatttg atttgatggc caaaaccccg tatatcgctc gccataaagg gaccccgctg     900
ttgcaacaaa ttgatacggc attagtgctg caacgcgatg cccaagggca aacactgccg     960
ctgtcaccgc aaaccaaatt gctgttcctc ggcgggcatg acaccaatat tgctaatatc    1020
gctggtatgt aggggccaa ttggcaatta ccacagcaac ctgataatac cccgcctggt    1080
ggcggattag tctttgagct atggcagaac ccagataatc atcagcgcta tgtcgccgtg    1140
aaaatgttct atcaaacgat ggatcagctg cgaaatgccg agaaattaga tatgaaaaac    1200
aacccagcta aaattgttcc aattaccatt gaaggttgtg agaacgaggg tgataacaaa    1260
ctttgccaac ttgagacttt ccaaaagaaa gttgcccaag tgatcgagcc agcctgccat    1320
atttaa                                                              1326

<210> SEQ ID NO 12
<211> LENGTH: 1326
<212> TYPE: DNA
<213> ORGANISM: Artificial Sequence
<220> FEATURE:
<223> OTHER INFORMATION: VARIANT Gene

<400> SEQUENCE: 12
```

```
atgtcagttg caaagagaaa tctgcactta tccgcactca ctttgataat gggctgtttt    60
accgcaggtg ctgccccgat tgctacaccg ccggccagct acacattaga gcgtgtggtt   120
attttgagtc gacatggtgt tcgctccccg acaaaacaaa cccagctaat gaatgatgtc   180
acacctgata aatggcccct gtggccagta aaagcgggct atttaacacc gcgaagggct   240
gagttagtga ctttgatggg gggattttat ggtgattatt ccgcagcca agggttgttg   300
tctgcggggt gtccggtaga tggctccgtt tatgcacagg cagatgttga ccaacgaacc   360
cgcttaaccg gacaggcatt cttggatggg atcgcaccgg attgtggtct gaaagtacat   420
tatcaggctg atttgaagaa agttgacccg ctatttcata ccgtcgaagc gggggtctgt   480
aaactggact cagcgaaaac tcatcaggct gttgaggagc gattgggcgg gccattgagt   540
gatcttagcc agcgctatgc caaacccttt gctcagatgg gcgaagtgct gaattttgca   600
gcatcgcctt attgcaagtc attgcaaaaa aatggaaaaa cctgtgattt tgcaactttt   660
acggcaaatg aaattaaggt aaacgaacgt ggtactaaag tttctctgag tgggccattg   720
gcactatcgt cgacattggg tgaaattttc ctgttacaag actcacaagc tatgccggat   780
gtggcctggc atcggctcag cggtgaagag aactgggttt cgctattgtc gttgcgcaat   840
gcgcaatttg atttgatggc caaaaccccg tatatcgctc gccataaagg acccgctg    900
ttgcaacaaa ttgataccgc attagtgctg caacgcgatg cccaagggca aacactgccg   960
ctgtcaccgc aaaccaaatt gctgttcctc ggcgggcatg acaccaatat tgctaatatc  1020
gctggtatgt tagggccaa ttggcaatta ccacagcaac ctgataatac cccgcctggt  1080
ggcggattag tctttgagct atggcagaac ccagataatc atcagcgcta tgtcgccgtg  1140
aaaatgttct atcaaacgat ggatcagctg cgaaatgccg agaaattaga tatgaaaaac  1200
aacccagcta aaattgttcc aattaccatt gaaggttgtg agaacgaggg tgataacaaa  1260
ctttgccaac ttgagacttt ccaaaagaaa gttgcccaag tgatcgagcc agcctgccat  1320
atttaa                                                             1326
```

<210> SEQ ID NO 13
<211> LENGTH: 29
<212> TYPE: DNA
<213> ORGANISM: Artificial Sequence
<220> FEATURE:
<223> OTHER INFORMATION: synthesized primer

<400> SEQUENCE: 13
cgcgaattcg ccccgattgc tacaccgcc                                      29

<210> SEQ ID NO 14
<211> LENGTH: 34
<212> TYPE: DNA
<213> ORGANISM: Artificial Sequence
<220> FEATURE:
<223> OTHER INFORMATION: synthesized primer

<400> SEQUENCE: 14
gatgcggccg cttaaatatg gcaggctggc tcga                                34

<210> SEQ ID NO 15
<211> LENGTH: 31
<212> TYPE: DNA
<213> ORGANISM: Artificial Sequence
<220> FEATURE:
<223> OTHER INFORMATION: synthesized primer

<400> SEQUENCE: 15
cgggggtctg taaaggcgac tcagcgaaaa c         31

<210> SEQ ID NO 16
<211> LENGTH: 31
<212> TYPE: DNA
<213> ORGANISM: Artificial Sequence
<220> FEATURE:
<223> OTHER INFORMATION: synthesized primer

<400> SEQUENCE: 16
gttttcgctg agtcgccttt acagaccccc g         31

<210> SEQ ID NO 17
<211> LENGTH: 31
<212> TYPE: DNA
<213> ORGANISM: Artificial Sequence
<220> FEATURE:
<223> OTHER INFORMATION: synthesized primer

<400> SEQUENCE: 17
cgggggtctg taaagcggac tcagcgaaaa c         31

<210> SEQ ID NO 18
<211> LENGTH: 31
<212> TYPE: DNA
<213> ORGANISM: Artificial Sequence
<220> FEATURE:
<223> OTHER INFORMATION: synthesized primer

<400> SEQUENCE: 18
gttttcgctg agtccgcttt acagaccccc g         31

<210> SEQ ID NO 19
<211> LENGTH: 31
<212> TYPE: DNA
<213> ORGANISM: Artificial Sequence
<220> FEATURE:
<223> OTHER INFORMATION: synthesized primer

<400> SEQUENCE: 19
ttaaggtaaa cgaaggcggt actaaagttt c         31

<210> SEQ ID NO 20
<211> LENGTH: 31
<212> TYPE: DNA
<213> ORGANISM: Artificial Sequence
<220> FEATURE:
<223> OTHER INFORMATION: synthesized primer

<400> SEQUENCE: 20
gaaactttag taccgccttc gtttacctta a         31

<210> SEQ ID NO 21
<211> LENGTH: 31
<212> TYPE: DNA
<213> ORGANISM: Artificial Sequence
<220> FEATURE:
<223> OTHER INFORMATION: synthesized primer

<400> SEQUENCE: 21
ttaaggtaaa cgaaccgggt actaaagttt c         31

<210> SEQ ID NO 22
<211> LENGTH: 31
<212> TYPE: DNA

```
<213> ORGANISM: Artificial Sequence
<220> FEATURE:
<223> OTHER INFORMATION: synthesized primer

<400> SEQUENCE: 22
gaaactttag tacccggttc gtttaccttaa a                              31

<210> SEQ ID NO 23
<211> LENGTH: 31
<212> TYPE: DNA
<213> ORGANISM: Artificial Sequence
<220> FEATURE:
<223> OTHER INFORMATION: synthesized primer

<400> SEQUENCE: 23
ttaaggtaaa cgaacgtggt actaaagttt c                               31

<210> SEQ ID NO 24
<211> LENGTH: 31
<212> TYPE: DNA
<213> ORGANISM: Artificial Sequence
<220> FEATURE:
<223> OTHER INFORMATION: synthesized primer

<400> SEQUENCE: 24
gaaactttag taccacgttc gtttaccttaa a                              31
```